(12) United States Patent
Wu et al.

(10) Patent No.: US 6,193,932 B1
(45) Date of Patent: Feb. 27, 2001

(54) STERILIZATION CONTAINER AND INSTRUMENT HOLDER THEREFOR

(75) Inventors: Su-Syin Wu, Irvine; Charles S. Bankert, Oceanside; Anahid Gamsarian, Fullerton; Abraham Merhazion, Tustin, all of CA (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/213,792

(22) Filed: Dec. 17, 1998

Related U.S. Application Data

(60) Provisional application No. 60/069,905, filed on Dec. 17, 1997.

(51) Int. Cl.[7] .................................................. A61L 2/16
(52) U.S. Cl. ........................... 422/28; 422/297; 422/300; 206/210; 206/370; 206/439
(58) Field of Search ............................. 422/28, 292, 297, 422/300; 206/205, 207, 210, 305, 363, 370, 438, 439

(56) References Cited

U.S. PATENT DOCUMENTS

| | | | |
|---|---|---|---|
| 4,262,799 | * | 4/1981 | Perrett .................................. 422/300 |
| 5,441,709 | * | 8/1995 | Berry, Jr. .............................. 422/300 |
| 5,492,671 | * | 2/1996 | Krafft .................................... 422/300 |
| 5,552,115 | * | 9/1996 | Malchesky ............................ 422/300 |
| 5,628,970 | * | 5/1997 | Basile et al. .......................... 422/300 |
| 5,843,387 | * | 12/1998 | Dane et al. ........................... 422/300 |

* cited by examiner

Primary Examiner—Robert J. Warden, Sr.
Assistant Examiner—Theresa T. Snider
(74) Attorney, Agent, or Firm—Andrew C. Farmer

(57) ABSTRACT

A sterilization container has an improved elastomeric instrument holder. The instrument holder comprises a panel of elastomer having a projection depending downwardly therefrom and received within an perforation through a perforated surface within the container to hold the panel thereto. An aperture through the panel is adapted for receiving and holding an instrument to be sterilized. An inner surface of the aperture is adapted to have a reduced area of contact with an instrument received within the aperture. For example, the surface may comprise chamfers which meet to form a sharp ridge which contacts the instrument. The contact surface may also be textured to reduce the area of contact with the instrument. Alternatively, the surface may be formed of a material which is sufficiently permeable to a sterilizing gas so as to allow the area of the instrument in contact with the surface to receive a sufficient amount of sterilizing gas to become sterilized.

19 Claims, 3 Drawing Sheets

STERILIZATION CONTAINER AND INSTRUMENT HOLDER THEREFOR

This application claims the benefit of U.S. Provisional Application No. 60/069,905 filed Dec. 17, 1997.

FIELD OF THE INVENTION

The present invention relates to holding instruments within a sterilization container.

BACKGROUND OF THE INVENTION

Sterilization containers for effecting instrument sterilization are well known in the art. Such containers may comprise a simple perforated box with a removable lid into which instruments are placed and which is then subsequently wrapped in a vapor transmissive, microorganism resistant material such as Central Supply Room ("CSR") wrap. Alternatively, the container may be sealed and be provided with ports covered with a vapor transmissive, microorganism resistant material. In either event, the prepared container is then placed into a sterilizer whereupon sterilizing gases pass through the container to sterilize the instruments contained therein. After the sterilization is complete, the vapor transmissive, microorganism resistant material prevents the instruments from being recontaminated. Typical sterilizing gases include: steam, hydrogen peroxide, ethylene oxide, chlorine dioxide peracetic acid and combinations thereof A plasma may be induced to enhance the sterilization process. These and other suitable sterilization schemes are well known to those of skill in the art.

Typically, the instruments to be sterilized are medical instruments, and many are quite delicate. To prevent them from being damaged, it is desirable to hold them within the container so that they do not collide with one another. Holders for this also enhance organization and prevent the instruments from covering other instruments to block the sterilizing gases from reaching all instruments.

One popular form of instrument holder comprises a piece of elastomeric material having an aperture which receives the instrument. Typically, the holder is vertically oriented with the instrument and aperture extending horizontally therethrough. Downwardly depending projections on the holder fit into a perforated portion of container to removably attach the holder to the container. Thus the holders can be arranged to accommodate varying instruments. The aperture in the holder typically intersects an upper edge of the holder creating a notch in the holder so that the instruments, especially long cylindrical instruments, can be inserted downwardly into the aperture and need not be threaded horizontally through the aperture.

One limitation of such systems is the high contact area between the instrument and the holder. To provide some rigidity to the holder, it is usually a thick panel of elastomer. If the aperture is a straight bore throughout the panel it creates a large inner surface to the aperture which contacts a correspondingly large surface of the instrument. Areas of contact between the instrument and holder may not receive sufficient sterilizing gas for complete sterilization. An alternative is to use a sheet metal panel in place of the panel or a wire like wrap which encircles the instrument. In the former, metal may cause damage to delicate instruments and since it is not elastomeric, it will not provide the elastomeric holding capability of the elastomeric holder. The wire like wraps require extra manipulation to encircle the instrument.

SUMMARY OF THE INVENTION

The present invention overcomes these and other limitations of the prior art by providing a sterilization container having an improved instrument holder. The sterilization container may take any form known by those of skill in the art but preferably comprises an enclosure having a perforated surface within with the instrument holder affixed to the surface. The instrument holder comprises a panel having at least one projection extending into a perforation through the surface to hold the panel to the perforated surface. An aperture through the panel is adapted to receive an instrument therethrough. The inner surface of the aperture is reduced in area to reduce contact between the instrument and the holder.

The area of contact may be reduced by chamfering the surface to produce a ridge which contacts the instrument. Preferably the ridge is sharp but may instead comprise a narrow radius curve. The instrument holder is preferably formed of a silicone elastomer. A slot may be provided from an upper surface of the holder into the aperture so that the instrument may be inserted radially into the aperture through the slot. Preferably, the slot has a narrower width than a diameter of the aperture whereby an instrument inserted therein may be retained more securely. The contact area may be further reduced by roughening the contact surface, preferably by structural texturing in a specific pattern, such as by providing a plurality of small protuberances within the aperture.

A method for sterilizing a surgical instrument according to the present invention comprises enclosing the instrument within a sterilization container which comprises an enclosure having an instrument holder therein. The instrument holder comprises a panel having at least one aperture therethrough. The aperture extends between first face second faces of the panel and is defined by an inner aperture surface between these two faces. The instrument is placed into the aperture into contact with the inner aperture surface and a sterilizing gas is admitted into the enclosure. The inner aperture surface is shaped to minimize contact with the instrument in the aperture and a portion of the instrument within the aperture between the first and second faces is contacted with the sterilizing gas.

Preferably, at least 40 percent of that portion of the instrument disposed within the aperture between the first and second faces is out of contact with the inner aperture surface and is contacted with the sterilizing gas in the contacting step, more preferably this percentage is at least 80 percent and most preferably at least 95 percent.

DETAILED DESCRIPTION

Figure 1:
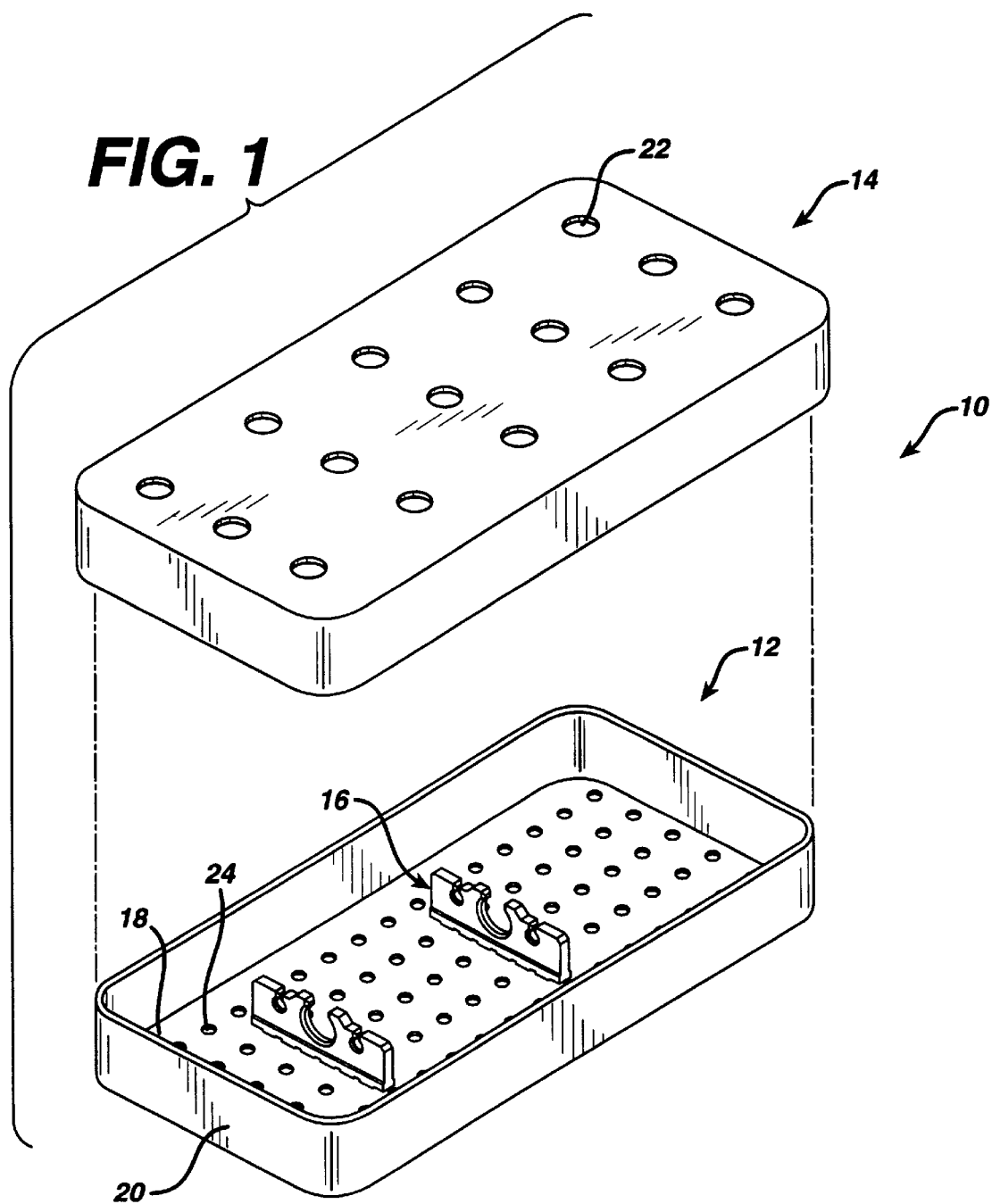
FIG. 1 is a perspective view of a sterilization container according to the present invention.

Turning now to the drawings and to FIG. 1 in particular, a sterilization container 10 according to the present invention comprises a base 12, lid 14 and plurality of instrument holders 16. The base 12 comprises a bottom panel 18 and upstanding sidewalls 20 giving the base an open box configuration. The lid 14 has a complementary structure to fit onto the base 12. A plurality of perforations 22 penetrate the lid to promote entry of sterilizing gases and an addition plurality of perforations 24 penetrate the bottom panel 18 to promote entry of sterilizing gases and also to drain liquid from the container.

The base 12 and lid 14 are preferably formed of a material capable of withstanding varying sterilization processes such as steam, hydrogen peroxide, peracetic acid, ethylene oxide, chlorine dioxide and the application of a plasma state. One particularly suitable class of materials comprises liquid crystal polymers. Preferably, the thermoplastic liquid crystal polymer comprises a wholly aromatic polyester. The liquid crystal polymer is preferably selected from the group consisting of: polybenzoate-naphthalate; polybenzoate-terephthalate-bisphenol-isophthalate; polybenzoate-terephthalate-ethylene glycol; and polynaphthalate-amino terephthalate. The liquid crystal polymer can be reinforced with a filler, such as glass, mineral fibers, or flouropolymers, in the form of powder, flakes or fibers. One commercially available example of a suitable liquid crystal polymer is the VectraR family produced by the Hoechst Celanese Corporation. Using thermoplastic, instead of thermosetting resins such as silicone rubber, eases processing and manufacturing.

Figure 2:
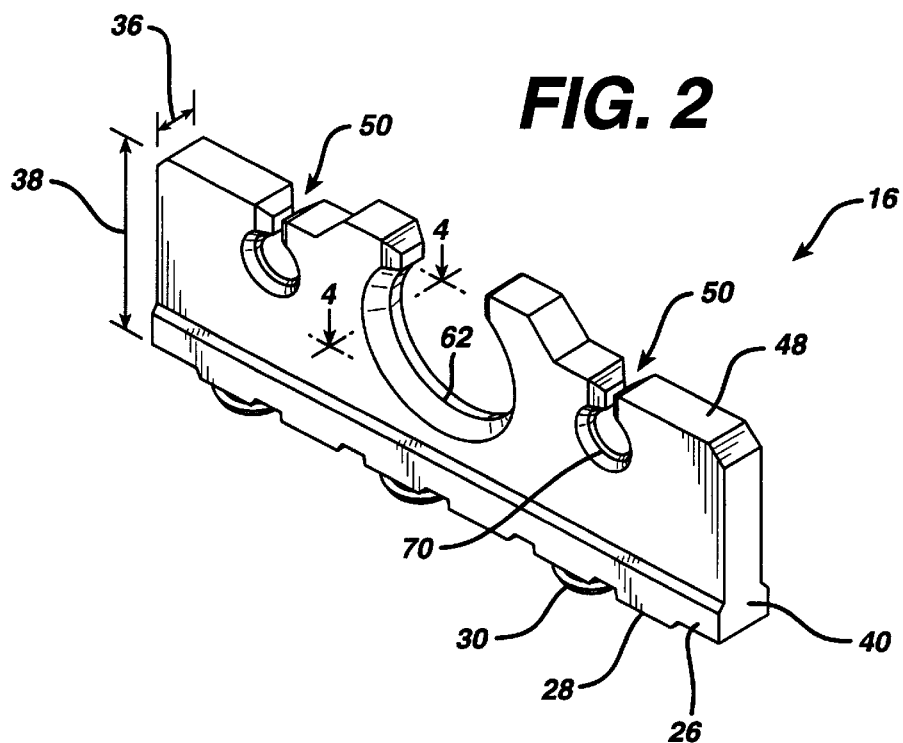
FIG. 2 is a perspective view of an instrument holder in the container of FIG. 1.
Figure 3:
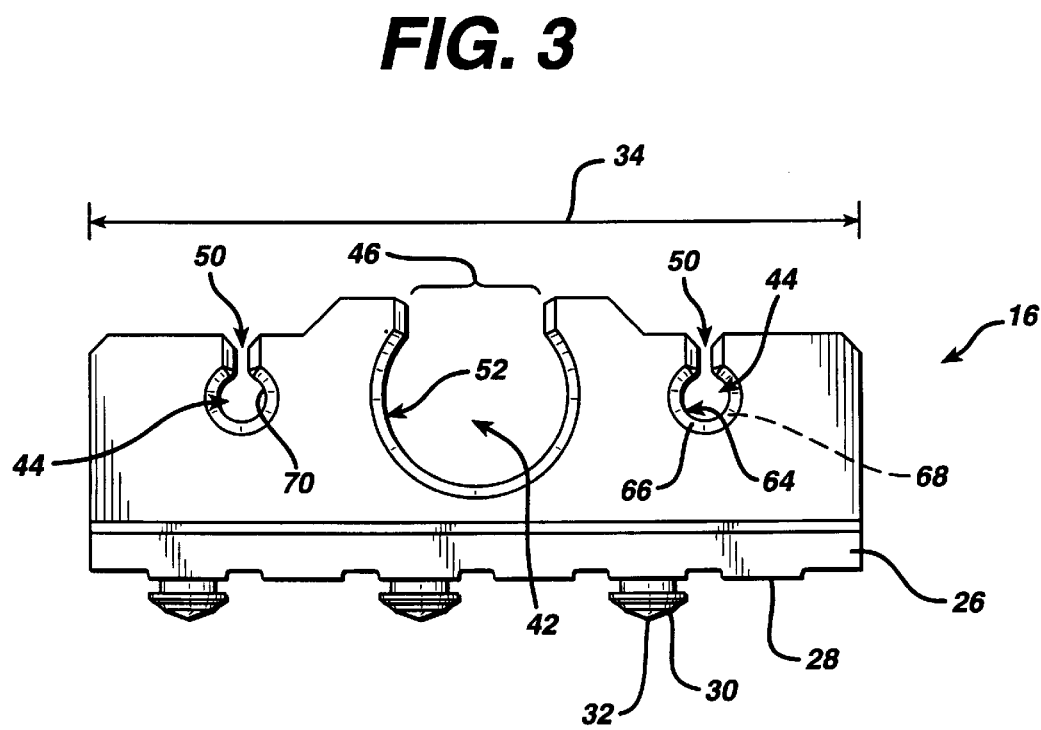
FIG. 3 is a front elevation of the instrument holder of FIG. 2.

FIGS. 2 and 3 illustrate in more detail one of the instrument holders 16. It is formed of a silicone elastomer. A lower surface 26 of the holder 16 has a plurality of pads 28 formed thereon which space the lower surface 26 from that which the holder 16 is attached, such as the bottom panel 18 of the container 10. A plurality of projections 30 depend from the lower surface, specifically from the pads 28. The pad enhances structural integrity of the instrument holder to the particular tray and profile. Each projection 30 is round and terminates in a conical barb 32. Each of the projections 30 pierces one of the perforations 24 in the base, with the barb 32 holding the projection 30 securely in place. FIG. 1 illustrates the projections 30 being received within the perforations 24 of the bottom panel 18 of the base 12. However, the instrument holder 16 can be attached to alternate surfaces. For instance, it can be attached to a separate perforated surface (not shown) within the base. It is popular in some sterilization container designs to incorporate a removable tray (not shown) for holding the instruments within the base 12 and the holder 16 can be affixed thereto. An example of such an enclosure is the Nichols U.S. Pat. No. 4,716,025, incorporated herein by reference.

The instrument holder 16 shown has a panel configuration, with an elongated length 34, narrow width 36 and a height 38 sufficient to accommodate a desired instrument (not shown in FIG. 2). It would be apparent to those of skill in the art that alternative configurations may be accommodated within the scope of the present invention. A base portion 40 of the instrument holder adjacent the pads 28 has a slightly wider thickness than the remainder of the holder 16 and provides some added rigidity.

One large aperture 42 and two smaller apertures 44 laterally penetrate the holder 16 (across the width dimension 36) and are adapted to receive instruments for sterilization. The large aperture 42 shown here is circular in shape and has a radius of 8.5 mm. The smaller apertures are also circular having radii of 2.8 mm. Of course, the size and shape of the apertures 42 and 44 may be altered to accommodate varying instrument sizes and shapes. For instance, the apertures 42 and 44 may be square or rectangular in shape to minimize points of contact with an instrument received therein. The size of the inner aperture is defined by the instrument size with additional gap space to prevent tight fitting, between instrument and the inner aperture.

A slot 46 leads vertically from a top surface 48 of the holder 16 into the larger aperture 42 and slots 50 lead vertically from the top surface 48 into the smaller apertures 44. The slots 46 and 50 allow instruments to be placed into the apertures 42 and 44 radially rather than having to thread the instrument coaxially through the apertures 42 and 44. Preferably, the slots 46 and 50 have a short length between the top surface 48 and their respective apertures 42 and 44 to enhance rigidity in that area, but the slots may be formed by intersecting the apertures 42 or 44 with the top surface 48 along a chord of the apertures to form a slot of zero length.

One objective of the present invention is to enhance the penetration of sterilizing gas to an instrument received in the apertures 42 and 44. In one embodiment this objective is achieved by forming the holder, at least at the area of the apertures 42 and 44, from a material the sterilizing gas can penetrate, as through permeation. For example, a silicone rubber, or a fluorinated silicone rubber, can be penetrated by hydrogen peroxide.

Figure 4:
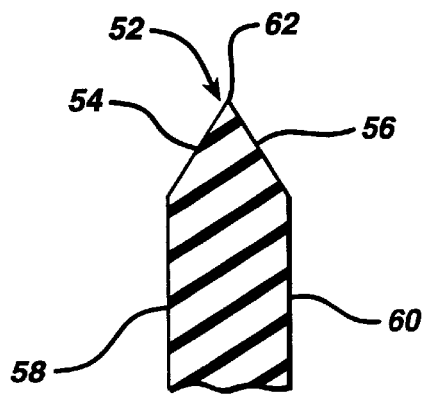
FIG. 4 is a sectional view taken along line 4—4 of FIG. 2 showing a contact surface comprising a sharp ridge in an aperture through the holder.
Figure 5:
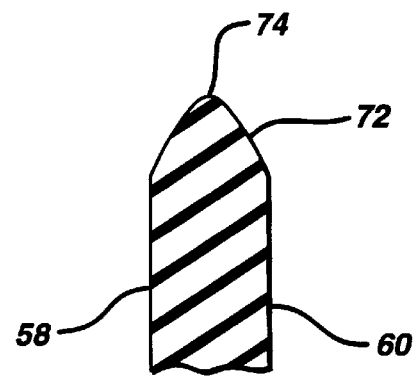
FIG. 5 is an alternative embodiment of the contact surface of FIG. 4, wherein a radius is added to the ridge to reduce possible stress concentration.

Alternatively, reducing contact between an instrument received within the apertures 42 and 44 and the holder 16 reduces areas which may receive inadequate sterilizing gas during the sterilization procedure. The primary area of contact is with an inner surface 52 of the aperture 42. If the aperture 42 passed through the holder 16 with a straight bore as in prior instrument holders, it would leave a large area of contact with the instrument. Turning to FIG. 4, the inner surface 52 reduces the contact surface. It comprises a first chamfer 54 and second chamfer 56 which extend from a first lateral face 58 and second lateral face 60, respectively, to meet and form a sharp ridge 62. A right angle intersection of the two chamfers provides a relatively rigid holding surface with minimal contact. To improve rigidity, the chamfers need not be straight, but may curve toward each other, as shown by the curved surface 72 of FIG. 5, to form a central ridge 4 having a narrow radius of curvature rather than a sharp edge.

The smaller apertures 44 are shown with an inner surface 64 defined by a first chamfer 66 and a second chamfer 68 which fail to meet and are connected by a short straight bore 70, approximately half the width of the holder width 36. Nevertheless, the area of contact with an instrument is less than with a full straight bore.

Figure 6:
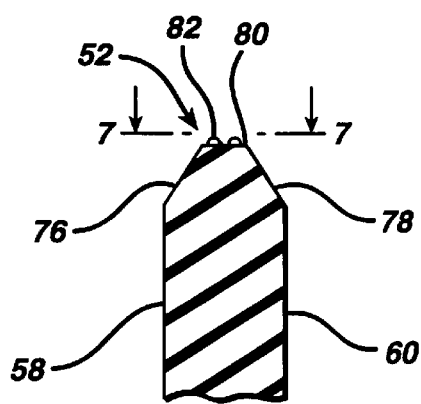
FIG. 6 is a further alternative embodiment of the contact surface of FIG. 4.
Figure 7:
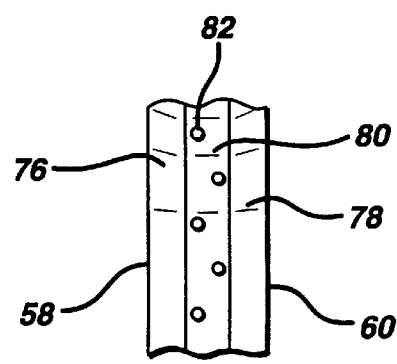
FIG. 7 is a side elevational view of the contact surface of FIG. 6

FIG. 6 shows a similar arrangement on the main aperture 42 in which a first chamfer 76 and second chamfer 78 extend from the first and second faces 58 and 60 but fail to meet and instead intersect a short straight bore section 80. To further reduce the area of contact, a plurality of hemispherical protuberances 82 are disposed thereon. Many different forms of texturing may be substituted therefor which achieve the end result of reducing the contact surface along the inner surface 52. For instance, the surface 80 may merely be roughened in such a fashion to enhance permeation of any gaseous sterilant between the surface 80 and an instrument (not shown) in contact therewith. In a particular, the mold surface can be roughened by EDM (electric-discharge machining) or chemical etching processes prior to molding.

As stated previously, the material from which the holder 16 is formed should withstand the temperature extremes and chemical environments of all major sterilization processes. Particularly suitable materials include: silicone rubber, fluorinated rubber, and thermoplastics. The preferred thermoplastics are thermoplastic elastomers such as, but not limited to, follows: Thermoplastic elastomeric olefins (TEOs), preferably EPR (ethylene-propylene rubber) and EPDM (ethylene-propylene diene rubber), tradename such as Santoprene by Advanced Elastomer Systems, and Styrene block copolymers, particularly those with soft olefin block, such as SEBS (styrene/ethylene-butylene/styrene), or SEPS (stryene/ethylene-propylene/styrene) with tradename such as Kraton by Shell Chemical or Styrenic-silicone block co-polyomers with tradename such as C-Flex. There are number of thermoplastics can be used for this application, such as, but not limited to, polyolefins, fluorinated polyolefins, chlorinated-fluorinated polyolefins, and liquid crystal polymers. The non elastomeric thermoplastics are more rigid (higher flex modules) but can be used with design modification within the ordinary skill in the art. It is especially advantageous to use thermoplastics, including thermoplastic elastomers, due to the ease of processing. Thermosetting resins such as silicone, rubber and fluorinated silicone rubber, requires many preparatory steps. Such as milling or pre-mixing. After molding, a post-curving may be required to eliminate volatile low molecular weight fractions. The selection of the best material for a particular design can be achieved within the ordinary skill in the art.

Various modifications and alterations of this invention will be apparent to those skilled in the art without departing from the scope and spirit of this invention. It should be understood that the invention is not limited to the embodiments disclosed herein, and that the claims should be interpreted as broadly as the prior art allows.

What is claimed is:

1. A sterilization container comprising:
   an enclosure;
   a perforated surface within the enclosure comprising a plurality of perforations through the surface; and
   an instrument holder affixed to the surface, the instrument holder comprising:
      a panel;
      at least one aperture through the panel, whereby an instrument may be placed through the aperture for holding the instrument; and
      wherein the panel has a first face and a second face with the at least one aperture extending therebetween, the aperture being defined by an inner aperture surface between the panel first face and panel second face and wherein the inner aperture surface has a contact surface against which the instrument received within the aperture can contact and wherein said contact surface has an area less than the inner aperture surface and wherein the inner aperture surface comprises a first chamfer extending from the first face, tapering toward the second face and terminating in a ridge, whereby the contact surface is limited to the ridge.

2. A sterilization container according to claim 1 wherein the ridge is formed by the intersection of the first chamfer and another surface so as to form the contact surface as being substantially linear.

3. A sterilization container according to claim 2 wherein the inner aperture surface further comprises a second chamfer extending from the second face and wherein the first chamfer terminates at and intersects with the second chamfer to form the ridge.

4. A sterilization container according to claim 1 where in the holder is formed of material selected from the following group:

silicone rubber, fluorinated rubber, thermoplastic elastomeric olefins, styrenic block copolymers, fluorinated polyolefins, chlorinated-fluorinated polyolefins, and liquid crystal polymers.

5. A sterilization container according to claim 1 wherein the panel has a third face between its first and second face and wherein a slot leads from the third face to the aperture whereby an instrument may be inserted radially into the aperture through the slot.

6. A sterilization container according to claim 5 wherein the at least one aperture has a diameter and the slot has a width in a plane with the aperture and the diameter of the aperture exceeds the width of the slot.

7. A sterilization container according to claim 1 wherein the inner aperture surface arcs in convex fashion from the first face to intersect the second face whereby to form the contact surface, the contact surface being substantially linear.

8. A sterilization container according to claim 1 wherein the panel has at least one projection depending therefrom into at least one perforation of the perforated surface to affix the panel thereto.

9. A sterilization container according to claim 8 wherein the panel has a width between the first face and the second face, and wherein the holder further comprises at least one pad adjacent to the at least one projection and abutting the perforated surface, the pad having a width exceeding the width of the panel.

10. A sterilization container according to claim 1 wherein the contact surface is no more than 40% of the area of the inner aperture surface.

11. A sterilization container according to claim 10 wherein the contact surface is no more than 20 percent of the area of the inner aperture surface.

12. A sterilization container according to claim 11 wherein the contact surface is no more than 5 percent of the area of the inner aperture surface.

13. An instrument holder for use with a sterilization container comprising:
   a panel having at least one projection thereon, the projection adapted to extend into a perforation in the sterilization container to hold the panel thereto;
   at least one aperture through the panel, whereby an instrument may be placed through the aperture for holding the instrument; and
   wherein the panel has a first face and a second face with the at least one aperture extending therebetween, the aperture being defined by an inner aperture surface between the panel first face and panel second face and wherein the inner aperture surface has a contact surface against which the instrument received within the aperture can contact and wherein said contact surface has an area less than the inner aperture surface and wherein the inner aperture surface comprises a first chamfer extending from the first face, tapering toward the second face and terminating in a ridge, whereby the contact surface is limited to the ridge.

14. An instrument holder according to claim 13 wherein the ridge is formed by the intersection of the first chamfer and another surface so as to form the contact surface as being substantially linear.

15. An instrument holder according to claim 13 wherein the instrument holder is formed of elastomeric silicone.

16. A method for sterilizing a surgical instrument comprising the steps of:
   enclosing the instrument within a sterilization container which comprises an enclosure, and an instrument holder within the enclosure, wherein the instrument holder comprises a panel having at least one aperture therethrough and wherein the panel has a first face and a second face with the at least one aperture extending therebetween, the aperture being defined by an inner aperture surface between the panel first face and panel second face;

placing the instrument into said aperture into contact with said inner aperture surface;

admitting a sterilizing gas into said enclosure; and adapting the inner aperture surface to enhance penetration of the sterilizing gas to a portion of the instrument within the aperture between the first and second faces by providing a chamfer extending from the first face, tapering toward the second face and terminating in a ridge which contacts the instrument and contacting said portion with the sterilizing gas.

17. The method according to claim 16 wherein at least 40 percent of that portion of the instrument disposed within the aperture between the first and second faces is out of contact with the inner aperture surface and is contacted with the sterilizing gas in the contacting step.

18. The method of claim 16 wherein at least 80 percent of that portion of the instrument disposed within the aperture between the first and second faces is out of contact with the inner aperture surface and is contacted with the sterilizing gas in the contacting step.

19. The method of claim 16 wherein at least 95 percent of that portion of the instrument disposed within the aperture between the first and second faces is out of contact with the inner aperture surface and is contacted with the sterilizing gas in the contacting step.

* * * * *